US008858071B2

(12) United States Patent
Emanuel et al.

(10) Patent No.: US 8,858,071 B2
(45) Date of Patent: Oct. 14, 2014

(54) METHOD AND APPARATUS FOR MONITORING MATERIALS

(75) Inventors: Michael Emanuel, Montreal (CA); Chongde Zhao, Mississisauga (CA); Biao Yu, Fredericton (CA); Dimitri Vinnik, Fredericton (CA); Chris Rendell, Hampton (CA)

(73) Assignee: C-Therm Technologies Ltd., Fredericton, New Brunswick (CA)

( * ) Notice: Subject to any disclaimer, the term of this patent is extended or adjusted under 35 U.S.C. 154(b) by 1939 days.

(21) Appl. No.: 11/721,720

(22) PCT Filed: Dec. 16, 2004
(Under 37 CFR 1.47)

(86) PCT No.: PCT/CA2004/002136
§ 371 (c)(1),
(2), (4) Date: Nov. 4, 2009

(87) PCT Pub. No.: WO2006/063427
PCT Pub. Date: Jun. 22, 2006

(65) Prior Publication Data
US 2011/0002356 A1 Jan. 6, 2011

(51) Int. Cl.
*G01N 25/18* (2006.01)
(52) U.S. Cl.
CPC .................................. *G01N 25/18* (2013.01)
USPC ............... 374/44; 374/102; 374/29; 436/149
(58) Field of Classification Search
USPC .............. 374/4, 5, 10–13, 57, 102–104, 107, 374/141, 153, 43–44, 29, 31–40, 30, 137; 340/588; 426/231; 436/147, 149; 422/51
See application file for complete search history.

(56) References Cited

U.S. PATENT DOCUMENTS

| | | | | | |
|---|---|---|---|---|---|
| 3,137,928 A | * | 6/1964 | Darrah et al. | ................. | 75/234 |
| 3,271,924 A | * | 9/1966 | Gramm et al. | ................. | 53/452 |
| 3,721,813 A | * | 3/1973 | Condon et al. | .................... | 702/1 |
| 4,102,750 A | * | 7/1978 | Nishihara et al. | ................ | 201/6 |
| 4,358,948 A | * | 11/1982 | Plessers | ......................... | 374/26 |
| 4,947,678 A | * | 8/1990 | Hori et al. | ................... | 73/54.42 |

(Continued)

FOREIGN PATENT DOCUMENTS

| | | | |
|---|---|---|---|
| FR | 2266320 A | * | 11/1975 |
| JP | 63193056 A | * | 8/1988 |
| WO | WO0160507 | | 8/2001 |
| WO | WO03002998 | | 1/2003 |

OTHER PUBLICATIONS

Supplemental Search Report dated Aug. 1, 2013, Application No. 04802311.3-1559 / 1831675 PCT/ CA2004002136, 5 pages.

*Primary Examiner* — Gail Verbitsky
(74) *Attorney, Agent, or Firm* — Anderson Gorecki & Rouille LLP

(57) ABSTRACT

A method and apparatus for monitoring during dynamic processes that determines when effective measurements of thermal effusivity and/or thermal conductivity can be made during a portion of a cycle during a calibration phase, then measures thermal effusivity and/or thermal conductivity during a subsequent dynamic process in dependence upon the time delay value and the measurement duration value until a desired value is obtained. A sensor having a measurement period of between one to two seconds allows monitoring of materials during dynamic processes such as tumbling, blending, mixing, and rocking. For example, measurements can be made until a value indicative of a desired mixture condition is obtained.

14 Claims, 6 Drawing Sheets

(56) References Cited

U.S. PATENT DOCUMENTS

| | | | |
|---|---|---|---|
| 4,952,535 A * | 8/1990 | Merkel | 501/98.4 |
| 5,064,294 A * | 11/1991 | Cerf et al. | 374/16 |
| 5,273,765 A * | 12/1993 | Weber et al. | 426/231 |
| 5,356,819 A * | 10/1994 | Ritschel | 436/147 |
| 5,795,064 A * | 8/1998 | Mathis | 374/44 |
| 6,031,025 A * | 2/2000 | Mercer et al. | 523/220 |
| 6,347,884 B1 * | 2/2002 | Faure et al. | 374/45 |
| 6,365,236 B1 * | 4/2002 | Maloney | 427/585 |
| 6,394,646 B1 * | 5/2002 | Ringermacher et al. | 374/7 |
| 6,589,310 B1 * | 7/2003 | Opoku-Adusei et al. | 75/245 |
| 6,676,287 B1 * | 1/2004 | Mathis et al. | 374/1 |
| 7,318,004 B2 * | 1/2008 | Butterfield | 702/130 |
| 7,357,035 B2 * | 4/2008 | Liu et al. | 73/756 |
| 7,909,505 B2 * | 3/2011 | Alexandrov et al. | 374/10 |
| 8,043,703 B2 * | 10/2011 | Cornie et al. | 428/408 |
| 8,092,928 B2 * | 1/2012 | Schofalvi et al. | 428/699 |
| 8,236,212 B2 * | 8/2012 | Marc | 264/45.5 |
| 2003/0119197 A1 | 6/2003 | Bonne et al. | |
| 2003/0134920 A1 * | 7/2003 | Poisl et al. | 521/59 |
| 2005/0002435 A1 * | 1/2005 | Hashimoto et al. | 374/43 |
| 2006/0159950 A1 * | 7/2006 | Kunisada et al. | 428/689 |
| 2009/0233784 A1 * | 9/2009 | Schofalvi et al. | 501/127 |
| 2010/0091812 A1 * | 4/2010 | Louban et al. | 374/4 |
| 2011/0296771 A1 * | 12/2011 | Miller et al. | 52/171.3 |
| 2012/0042981 A1 * | 2/2012 | Ray et al. | 138/141 |

* cited by examiner

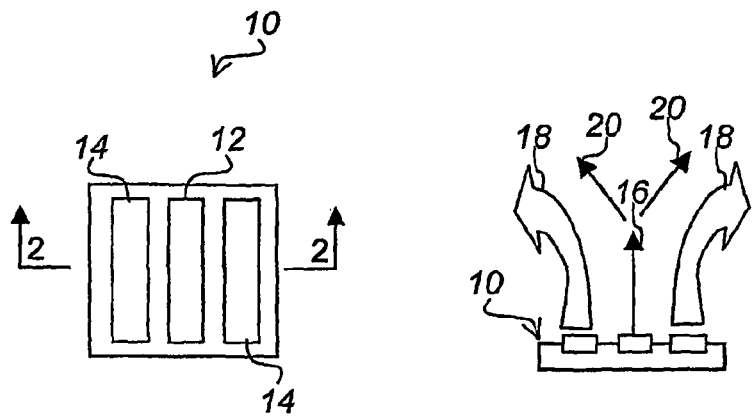
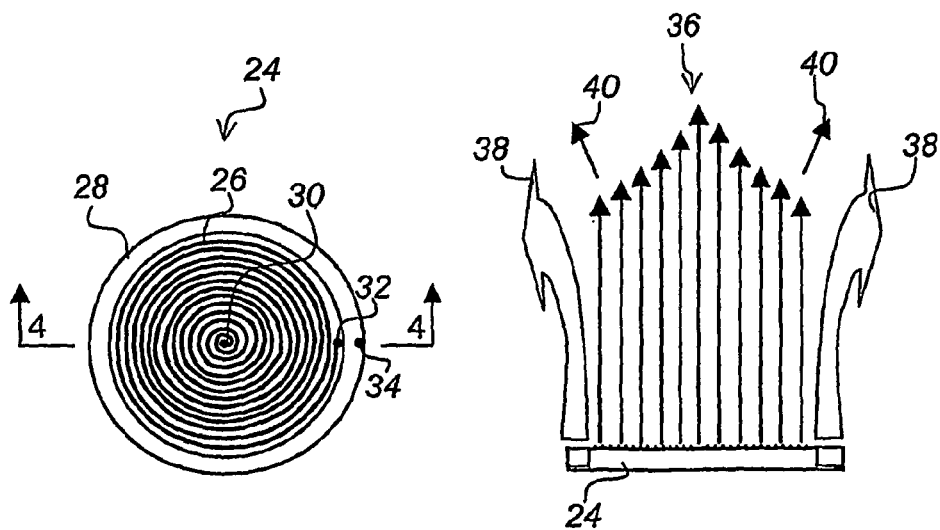
Fig. 1
Prior Art
Fig. 2
Prior Art
Fig. 3
Fig. 4

METHOD AND APPARATUS FOR MONITORING MATERIALS

Cross-Reference To Related Applications

This application is a 35 U.S.C. section 371 National Stage Entry of PCT/CA2004/002136 filed Dec. 16, 2004, which is incorporated by reference.

FIELD OF THE INVENTION

The present invention relates to methods and apparatuses for monitoring materials and is particularly concerned with monitoring during dynamic processes.

BACKGROUND OF THE INVENTION

A sensor for monitoring materials is taught in the applicant's U.S. Pat. No. 5,795,064, issued Aug. 18, 1998 to Mathis, the entire disclosure of which is hereby incorporated by reference. This sensor provides a non-destructive test due to the surface measurement and interfacial nature of the sensor interaction with the sample. The sensor measures a materials effusivity (the square root of thermal conductivity, density and heat capacity).

The sensor of the above identified patent can also be used for direct measurement of thermal conductivity as taught is the applicant's U.S. Pat. No. 6,676,287, the entire disclosure of which is hereby incorporated by reference.

Referring to FIG. 1 there is illustrated a known material monitoring sensor. The sensor 10 includes a hot wire 12 and guard heaters 14.

Referring to FIG. 2 there is illustrated heat flow from the sensor of FIG. 1.

In operation, a known quantity of electrical current is passed through the heating elements 12 and 14 of the sensor for a known time. This results in a temperature rise at the sensor/sample interface and, over time, a heat flow from the sensor into the sample. The sensor functions by measuring the temperature rise at the sensor/sample interface over time. The heat transfer properties of the sample profoundly affect the rate of this temperature rise. If the sample is a good thermal insulator, then as heating continues, very little heat is conducted away from the sensor/sample interface and the temperature at the interface rises very quickly. If the sample is a good heat conductor, then as the heating continues, the heat is conducted away from the sensor/sample interface and the temperature at the interface rises very slowly.

The heating elements and control mechanisms are designed to keep the sensor/sample interface temperature rise within certain boundaries. Temperature rise can also be controlled by adjusting the test time. A calibration curve is constructed by performing tests on standard materials with known thermal effusivity and/or thermal conductivity. Once the calibration curve is determined, samples are tested under identical experimental conditions, and the rate of temperature change at the sensor/sample interface is translated directly into thermal effusivity and/or thermal conductivity.

The sensor for FIG. 1 uses tightly controlled heating at the surface of a sample to make direct measurements of thermal effusivity and/or thermal conductivity. The apparatus applies a known quantity of heat for a known time to the surface of a sample. During testing, three basic things happen to the applied heat: some of the heat goes into the backing material, most of the heat goes into the sample, and some of the heat goes nowhere and causes a localized temperature increase at the sensor/sample interface. The magnitude of the temperature rise at the sensor/sample interface can be quantitatively converted to thermal effusivity and/or thermal conductivity because the rise is completely dependent on the heat transfer properties of the material. As shown in FIG. 2, the heat flow from the hot wire 12 into a material being tested is initially straight as indicated by an arrow 16, due to the heat flow from the guard heaters 14 as indicated by curved arrows 18. However, the heat flow then diverges as indicated by arrows 20.

Consequently, the sensor is highly suitable for static measurements as the sensor must remain in stable contact with the material being measured. Unfortunately, many processes in which material measurements are desirable are dynamic in nature.

While providing a valuable tool for sample measurement, the sensor's structure and geometry result in a measurement period in the order of two to ten seconds. For processes such as mixing, using for example a V blender, the blender must be stopped in a particular orientation to allow the material being mixed to settle and to contact the sensor in order to take a reading. This results in a time delay for each measurement, which cumulatively adds to the total mixing time and actually disturbs the mixing process.

Consequently, there is a need in the prior art for a method and apparatus for monitoring materials during dynamic processes.

SUMMARY OF THE INVENTION

An object of the present invention is to provide an improved method and apparatus for monitoring materials.

In accordance with an aspect of the present invention there is provided apparatus for monitoring during a dynamic process comprising: means for measuring effusivity during a portion of a rotation period; means for determining inflection points therefrom; means for determining a time delay value and a measurement duration value from the inflection points; and means for measuring effusivity during a subsequent dynamic process in dependence upon the time delay value and the measurement duration value until a value indicative of a desired mixture condition is obtained.

In accordance with another aspect of the present invention there is provided a method of monitoring during a dynamic process comprising the steps of: measuring effusivity during a portion of a rotation period; determining inflection points therefrom; determining a time delay value and a measurement duration value from the inflection points; and measuring effusivity during a subsequent dynamic process in dependence upon the time delay value and the measurement duration value until a value indicative of a desired mixture condition is obtained.

In accordance with another aspect of the present invention there is provided an apparatus for monitoring during a dynamic process comprising: means for measuring thermal conductivity during a portion of a cycle; means for determining inflection points therefrom; means for determining a time delay value and a measurement duration value from the inflection points; and means for measuring thermal conductivity during a subsequent dynamic process in dependence upon the time delay value and the measurement duration value until a value indicative of a desired condition is obtained.

In accordance with another aspect of the present invention there is provided a method of monitoring during a dynamic process comprising the steps of: measuring thermal conductivity during a portion of cycle; determining inflection points therefrom; determining a time delay value and a measurement duration value from the inflection points; and measuring thermal conductivity during a subsequent dynamic process in dependence upon the time delay value and the measurement duration value until a value indicative of a desired condition is obtained.

The present invention advantageously provides a method and apparatus for monitoring materials dynamically during dynamic processes.

BRIEF DESCRIPTION OF THE DRAWINGS

The present invention will be further understood from the following detailed description with reference to the drawings in which:

FIG. 1 illustrates a known material monitoring sensor;

FIG. 2 schematically illustrates heat transfer from the sensor of FIG. 1;

FIG. 3 illustrates a material monitoring sensor in accordance with an embodiment of the present invention;

FIG. 4 schematically illustrates heat transfer from the sensor of FIG. 3;

DETAILED DESCRIPTION OF THE PREFERRED EMBODIMENT

Figure 5:
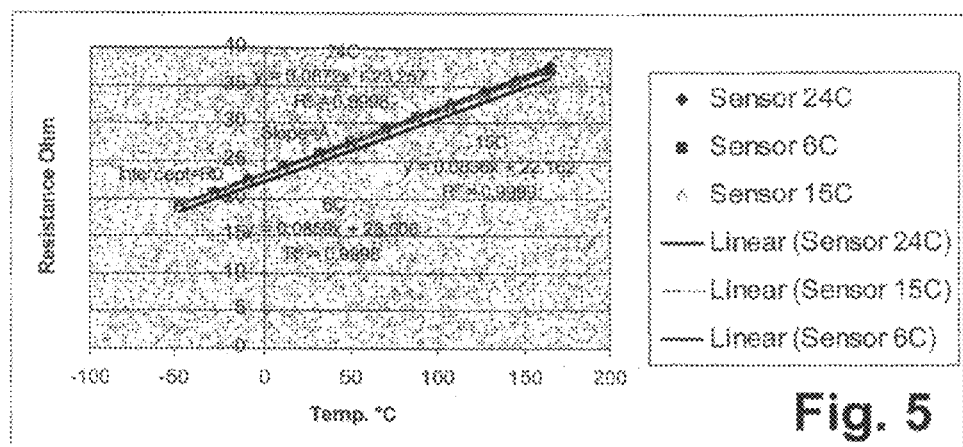
FIG. 5 graphically illustrates an example of a TCR calibration curve.

Referring to FIG. 3 there is illustrated a material monitoring sensor in accordance with an embodiment of the present invention. The sensor 24 has a circular geometry, a spiral heater 26 and an outer guard heater 28. Electrical power is provided to the sensor 24 via connections 30, 32 and 34. Hence, power to the spiral heater 26 is applied to connections 30 and 32, and power to the guard heater 28 is applied to connectors 32 and 34. The guard heater provides another heat source and may take the form of a separate wire or be integrated as part of the spiral heater.

When integrated, there are three inflection points on the heater wire. One in the center 30, another some distance away from the centre 32, representing an end of the spiral heater 26 and the start of the guard heater 28, and the last at the end of the wire 34 denoting the other end of the guard heater 28. For simplicity of the drawing and to take into account that the guard heater 28 may take different forms, the guard heater 28 is shown as a annular ring surrounding the spiral heater 26.

The sensor 24 can be made as a thin film resistor or thick film resistor material on ceramics or other substrate material. This resistor material typically has a resistance in the range of a few ohms up to hundreds of ohms and thus requires a current in the range of 50-150 milliamps, for example. The resistance can be changed by varying the density of the geometry of the coils, the width and other process parameters. The coiled configuration of the sensor provides greater depth for sensing. For example the sensor 24 can be made using thick film technology, having an alumina (aluminum oxide) base, and platinum wires enclosed in glass cover (not shown in FIG. 3). Optionally, the sensor includes a low-adhesion coating, for example Teflon (a trademark of DuPont) to provide encapsulation and resistance to acids and other materials.

While a circular sensor with a spiral heater is shown in the drawings, the sensor can have other shapes, for example, a rectangular, hexagon, octagon, or other similar closed polygons. Similarly the particular arrangement of heater tracks can also be changed from spiral to serpentine or similar arrangements. The main consideration is provision of a substantially uniform distribution over the area of the heater.

In operation, the guard heater 28 provides more heat (to compensate for the heat loss in two directions), hence is tuned to do so regardless of whether its form is separate or integrated as an extension of the spiral heater.

Referring to FIG. 4 there is illustrated schematically heat transfer from the sensor of FIG. 3. In operation, the sensor 24 generates heat flow as represented by arrows 36 from the spiral heater 26 and heat flow as represented by curved arrows 38 from the guard heater 28. The spiral heater acts as a distributed heat source providing a substantially parallel heat flow 36 to a much greater depth than the prior art sensor 10 before dispersing as represented by arrows 40.

As a result of the configuration of the sensor 24, this type of sensor can be used for measuring the thermal effusivity of solids as well as powders, liquids, and gases. The sensor 24 is also able to measure the effusivity of a vacuum. Consequently, calibration can be done with just two measurements, vacuum and only one material. This leads to less errors because the sensor calibration is no longer distorted by environmental factors (humidity, barometric pressure), material (impurities in the sample) and quality of the contact between the sensor and the material (true for vacuum only). This also reduces the number of materials required for calibration to one.

The temperature coefficient of resistivity (TCR) calibration is calibration of sensor resistance versus temperature, and is given in this equation (assuming perfect linearity):

$$R = R_0 + A \cdot T \tag{1}$$

Where:
R=resistance of sensor at a given temperature (ohms)
$R_0$=resistance of sensor at 0° C. (ohms)
T=temperature (° C.)
A=slope (ohm/° C.)

An example of a TCR calibration curve is shown in FIG. 5. For a sensor 24 the following are typically observed:
Range of A~0.05-0.15 ohm/° C.
Range of $R_0$~20-25 ohm
The slope A is equal to:

$$A = R_0 \cdot TCR \tag{2}$$

Where: TCR=Temperature Coefficient of Resistivity, assumed to be constant over the measured temperature range.

The slope depends on sensor resistance in general, and on $R_0$ in particular. Therefore, even if two sensors have the same TCR, their temperature calibration lines will still have different slopes if their resistance at a given temperature is not the same. The higher slope, the more sensitive is the sensor. In other words, higher TCR and higher sensor resistance provide higher sensitivity.

For platinum used in the sensor 24, the TCR is approximately 0.0035° C.$^{-1}$, or 0.35% for each ° C.

To calculate the surface temperature of the sensor from (1) use:

$$T = \frac{R - R_0}{A} \quad (3)$$

The resistance may be measured directly by the electronics (using very low current and short time to avoid sensor heating), or calculated from the initial voltage, $V_0$, or from the applied power P (if applied power is the same for all sensors).

$$R = \frac{V_0}{I} \quad (4)$$

$$R = \frac{V_0^2}{P} \quad (5)$$

Where R is the measured sensor resistance at the said temperature, I is the current and P is the power.

Basic 2 or 3-Point Effusivity Calibration

The theoretical solution of the heat equation in the case of pure one-dimensional flow of heat from the sensor (material 1) to the measured material (material 2) at the interface between the materials follows this equation:

$$\Delta T \propto \frac{G\sqrt{t}}{Eff_1 + Eff_2} \quad (6)$$

Where: $\Delta T$ = change in surface temperature (° C.)

$G$ = power flux supplied to sensor (W/m$^2$)

$t$ = time measured from start of process (sec)

$Eff_1$ = equivalent effusivity of sensor $\left(\frac{W\sqrt{s}}{m^2 k}\right)$ $Eff_2$ = effusivity of measured material $\left(\frac{W\sqrt{s}}{m^2 k}\right)$ Assumption: Both sensor and measured material are in equilibrium and at the same temperature when the measurement starts.

Note: Constants are ignored in equation (6).

In the previous section we saw the connection between sensor temperature and resistance. The resistance change of the sensor is:

$$\Delta R = R - R_0 = A \cdot \Delta T \quad (7)$$

And the voltage change on the sensor is:

$$\Delta V = I \cdot \Delta R = I \cdot A \cdot \Delta T \quad (8)$$

Using equation (6) we can write:

$$\Delta V \propto \frac{I \cdot A \cdot G \sqrt{t}}{Eff_1 + Eff_2} \quad (9)$$

Figure 6:
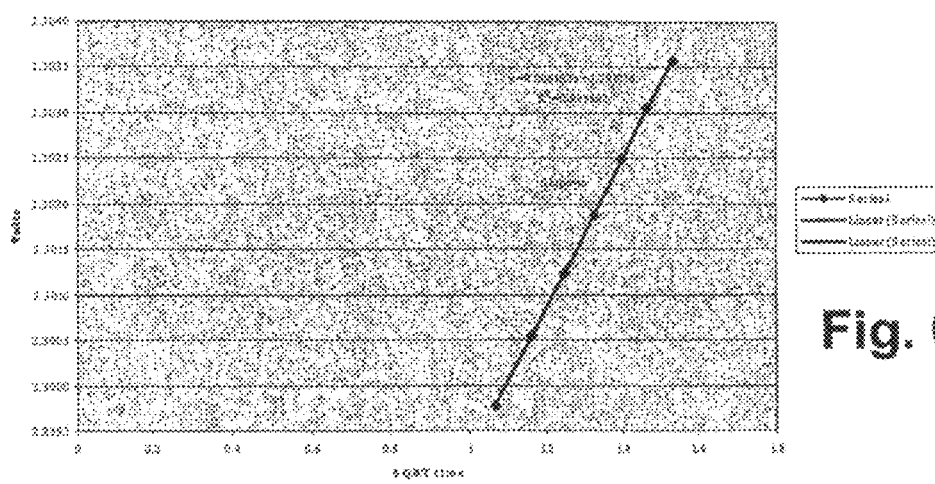
FIG. 6 graphically illustrates an example of a voltage versus √t measurement.

A example of voltage versus √t measurement is graphically illustrated in FIG. 6.

Equation (9) can be written (in the linear zone) as:

$$\Delta V \propto m \sqrt{t} \quad (10)$$

Where m is the slope, $$m = \frac{I \cdot A \cdot G}{Eff_1 + Eff_2} \quad (V/\sqrt{s}) \quad (11)$$

$$\frac{1}{m} = \frac{Eff_1 + Eff_2}{I \cdot A \cdot G} \quad (\sqrt{s}/V) \quad (12)$$

If $Eff_2$ is 0, i.e. sensor response is measured in vacuum, then:

$$\frac{1}{m}(\text{vacuum}) = \frac{Eff_1}{I \cdot A \cdot G} \quad (13)$$

The expression $Eff_1/IAG$ is a sensor/system expression of merit, and depends only on sensor characteristics and supplied power, and may be used for calibration.

Figure 7:
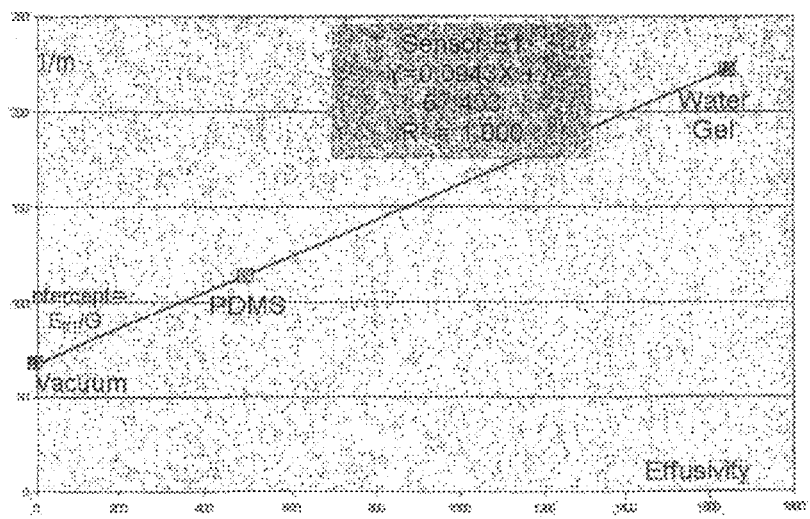
FIG. 7 graphically illustrates an example of a sensor effusivity calibration curve using vacuum and other materials.

FIG. 7 graphically illustrates an example of sensor effusivity calibration curve using vacuum and other materials. The calibration line shows very good linearity.

The calibration line can be written as:

$$\frac{1}{m} = M \cdot Eff_2 + C \quad (14)$$

Where M is the slope of the effusivity calibration and is equal to:

$$M = \frac{1}{I \cdot A \cdot G}(m^2 \cdot ° \text{ C.}/W \cdot Amp \cdot \Omega) \quad (15)$$

And C is:

$$C = \frac{Eff_1}{I \cdot A \cdot G} \quad (\sqrt{s}/V) \quad (16)$$

Note that C is the 1/m value when $Eff_2$ is zero, i.e. for vacuum.

To calculate the effusivity of the measured materials from (14) we use:

$$Eff_2 = \frac{\frac{1}{m} - C}{M} \quad (17)$$

Where 1/m is the inverse of the voltage versus √t slope measured for this material, and M & C are the slope and intercept of the effusivity calibration curve for that sensor.

Range typical for this present sensor design and system.
M=0.07-0.1 (m$^{2}\cdot°$ C./W·Amp·Ω)
C=40-80 ($\sqrt{s}$/V)

1-Point Effusivity Calibration

We have mentioned above that vacuum is used in the sensor effusivity calibration process. But a single point is not enough, so one or more materials are used as well (PDMS (polydimethylsiloxanes) and possibly water gel) to create the calibration line. The vacuum measurement is relatively stable because it is not prone to material variations. However, the other calibration points may be affected by temperature and other environmental conditions. Since different sensors may be calibrated at different times and conditions, offset errors in calibration lines are quite common between sensors. These offset errors may be typically in the order of 1-5%.

We can reduce the relative measurement errors (or % RSD) between sensors measuring the same material by applying a 1-point calibration process.

Since the sensor calibration curve has two parameters, M & C, we may recalculate either one of them to match all sensors such that the calculated effusivities of all sensors, measuring the same uniform material at the same time and conditions, are identical. Since the parameter C is inherent to the sensor/system, and is the measured 1/m value in vacuum, it is inherently more accurate than the parameter M, which is created from both C and measurements of the calibration materials. Therefore, we are inclined to alter M for the 1-point calibration rather than altering C.

The 1-point calibration process takes a few measurements, done by different sensors on the same material at the same time, recalculates each sensor's M such that all sensors provide the same calculated effusivity number, and displays the new calculated effusivities for each sensor.

If sensor (1) has calibration parameters $M_1$ and $C_1$ and measures $1/m_1$, from equation (17) the calculated effusivity will be:

$$(\text{Eff}_2)_1 = \frac{\frac{1}{m_1} - C_1}{M_1} \quad (26)$$

Similarly for sensor (2) with $M_2$, $C_2$, and $1/m_2$:

$$(\text{Eff}_2)_2 = \frac{\frac{1}{m_2} - C_2}{M_2} \quad (27)$$

Because of the reasons mentioned above, $(\text{Eff}_2)_1$ differs somewhat from $(\text{Eff}_2)_2$. To equalize them to the latest value we may change only $M_1$, or alternatively we may change both $M_1$ and $M_2$ to bring the effusivity value to another desired value, or to the average between the values of $(\text{Eff}_2)_1$ and $(\text{Eff}_2)_2$. Once the effusivities are recalculated with the modified M(s), both sensors show the same number.

The 1-point calibration corrects only the offset error between sensors, but cannot correct the variance of each individual sensor. Therefore, the improvement provided by the 1-point calibration is limited by this variance (excluding the case where the variance of different sensors is correlated).

The 1-point calibration corrects the variance between sensors at certain measurement conditions and material, by altering the effusivity calibration line. One must be careful to not apply the new calculated slopes from one material to another, as this may increase the variance between sensors and adversely affect the accuracy. Rather, the 1-point calibration process must be repeated for different materials and conditions.

Calibration can be done on a major component of the mix or on the expected value of the mix.

Figure 8:
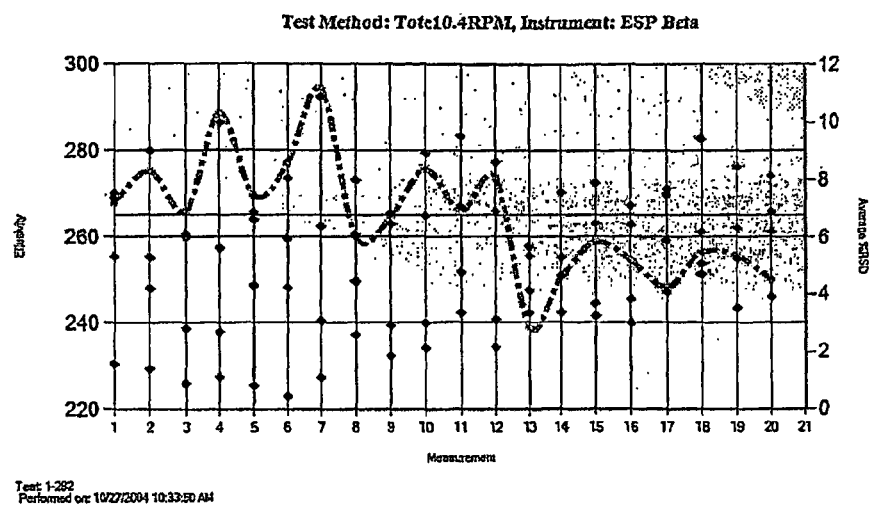
FIG. 8 graphically illustrates an example of early dynamic measurements before 1-point calibration.
Figure 9:
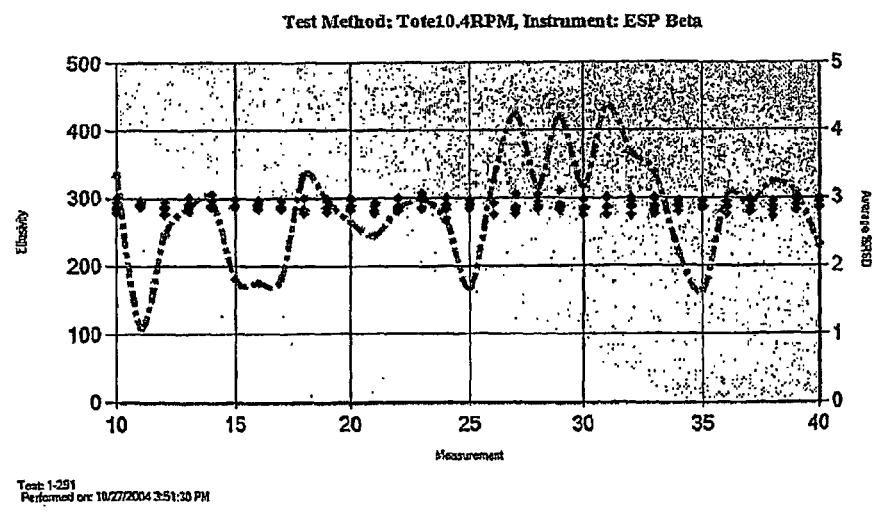
FIG. 9 graphically illustrates an example of early dynamic measurements after 1-point calibration.

FIGS. 8 and 9 show early dynamic measurements before and after 1-point calibration. RSD of 3-11% improved to 1-5%, approximately two times tighter.

Figure 10:
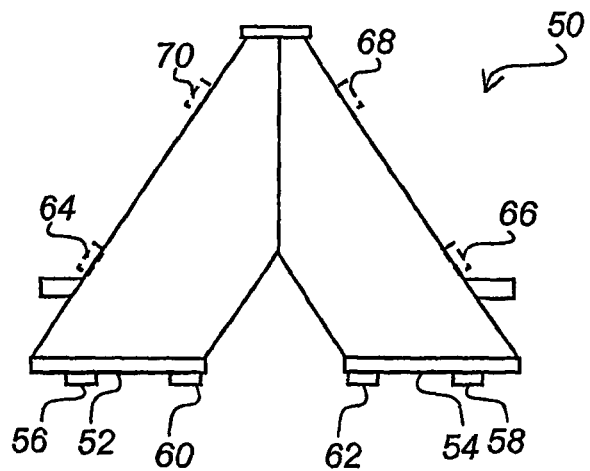
FIG. 10 schematically illustrates a V blender having the sensors of FIG. 3.

Referring to FIG. 10 there is graphically illustrated a V blender having the sensors of FIG. 3. In a typical implementation of a measurement system using the sensors of FIG. 3 a plurality of sensors are placed in different positions on the V blender 50. For example, on the blender lids 52 and 54 outer sensors 56 and 58 could be positioned along with inner sensors 60 and 62. Optionally other sensors 64, 66, 68, and 70 could be placed within the V blender. While a V blender is shown in FIG. 10, the sensors can also be fitted to other types of blenders, for example a bin blender.

Figure 11:
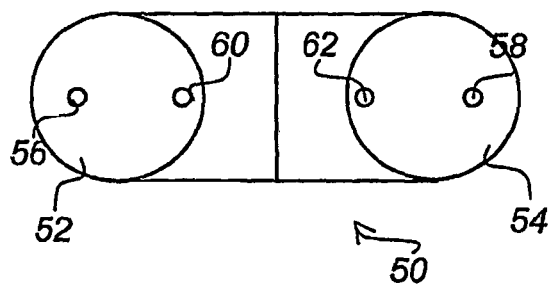
FIG. 11 schematically illustrates a top view of the V blender of FIG. 10.

Referring to FIG. 11 there is illustrated schematically a top view of the V blender of FIG. 10. This view shows the blender lids 52 and 54 with outer sensors 56 and 58 and inner sensors 60 and 62.

Figure 12:
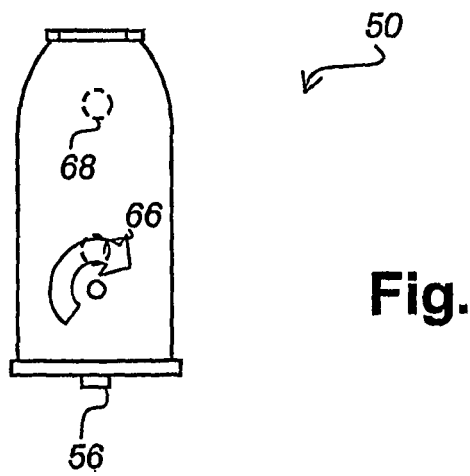
FIG. 12 schematically illustrates an end view of the V blender of FIG. 10.

Referring to FIG. 12 there is illustrated schematically an end view of the V blender of FIG. 10.

Figure 13:
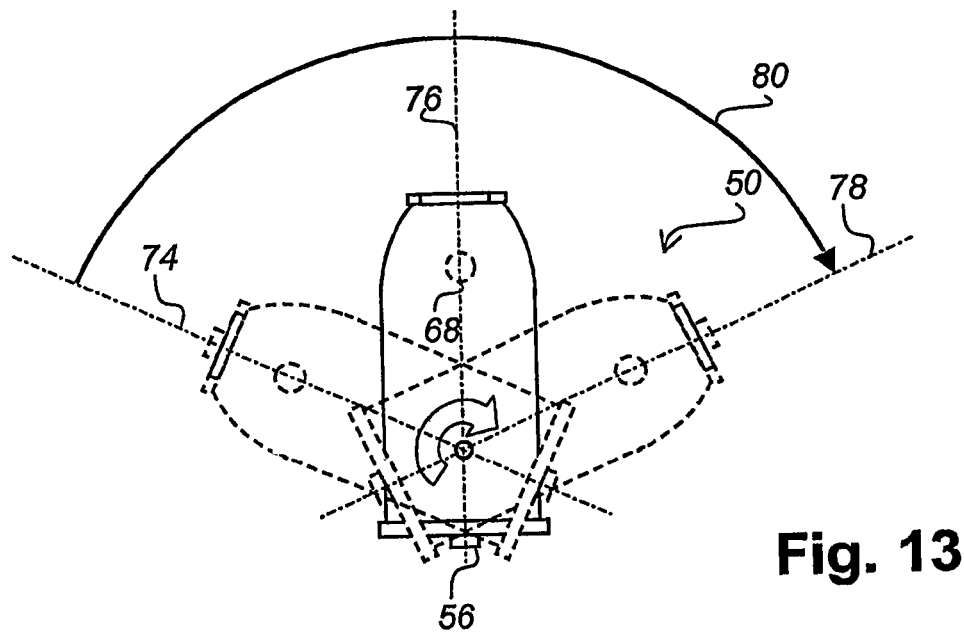
FIG. 13 schematically illustrates the end view of FIG. 12 with two rotational positions thereof superimposed.

Referring to FIG. 13 there is illustrated schematically the end view of FIG. 12 with two rotational positions thereof superimposed. The V blender is illustrated rotating from a first position along axis 74 through a second position with axis 76 to a third position with axis 78 during a clockwise rotation through a arc 80. If sensors are located in the lids 52 and 54 as sensors 56, 58, 60 and 62 are, or if positioned as shown by optional sensors 64 and 66, then the arc 80 represents a period of time when the sensors would likely be covered by stable material. The arc 80 therefore represents a potential measurement period for sensors 56, 58, 60, 62 and optional sensors 64 and 66.

Figure 14:
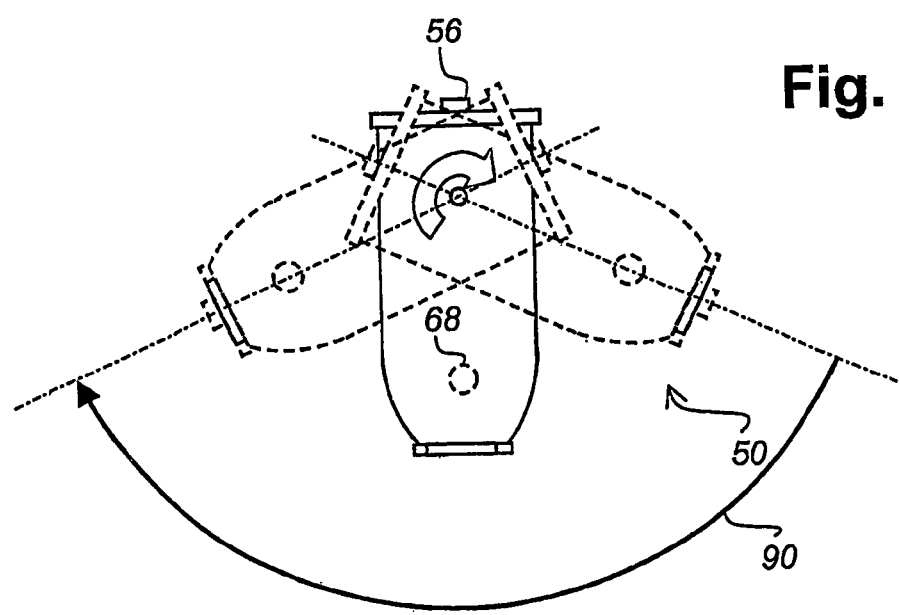
FIG. 14 schematically illustrates an inverted end view of FIG. 12 with two rotational positions thereof superimposed.

Similarly, referring to FIG. 14 there is illustrated schematically illustrates an inverted end view of FIG. 12 with two rotational positions thereof superimposed. The V blender is illustrated rotating clockwise through a arc 90. If sensors are located as sensors 68, and 70 are, then the arc 90 represents a period of time when the sensors would likely be covered by stable material. The arc 90 therefore represents a potential measurement period sensors 68 and 70.

A synchronization map of delays from a known point in the rotation to turning on of a sensor or group of sensors can be used to take full advantage of measurement periods during a given rotation. Such a mapping can be generated based on rotation speed and sensor location.

However, the precise positioning of a usable measurement period also depends upon percentage fill of the blender and the properties of the materials being mixed.

Hence it is desirable to measure a long sensor response, and show the inflection points caused by, for example, moving powder. In order to do this a reproducible blender orientation signal is required that provides a per rotation reference point to initiate timing of the sensor delays. For example an accelerometer chip can be used to generate a pulse for a particular orientation of the blender. The computer then uses this pulse as a reference point. This helps to establish an exact synch map and other useful parameters of the particular blender, fill level and RPM.

Figure 15:
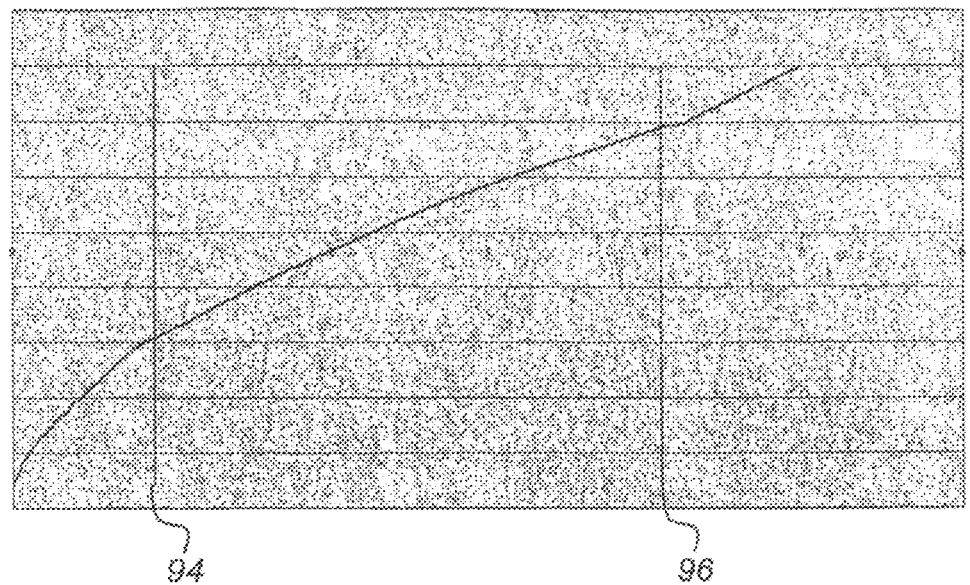
FIG. 15 graphically illustrates an example of a five-second measurement with one of four sensors is shown in FIG. 11.

Referring to FIG. 15, there is graphically illustrated an example of a five-second measurement (~80% of a complete revolution at 10 RPM) of a blender in motion with four sensors is shown in FIG. 11. For one sensor there are two inflection points about 3 seconds apart, caused by the moving powder, as indicated by lines 94 and 96. These measurements can then be used to manually establish delay values in a synchronization map or can be used by a computer programmed to determine the inflection points and then automatically calculate an appropriate measurement period.

Figure 16:
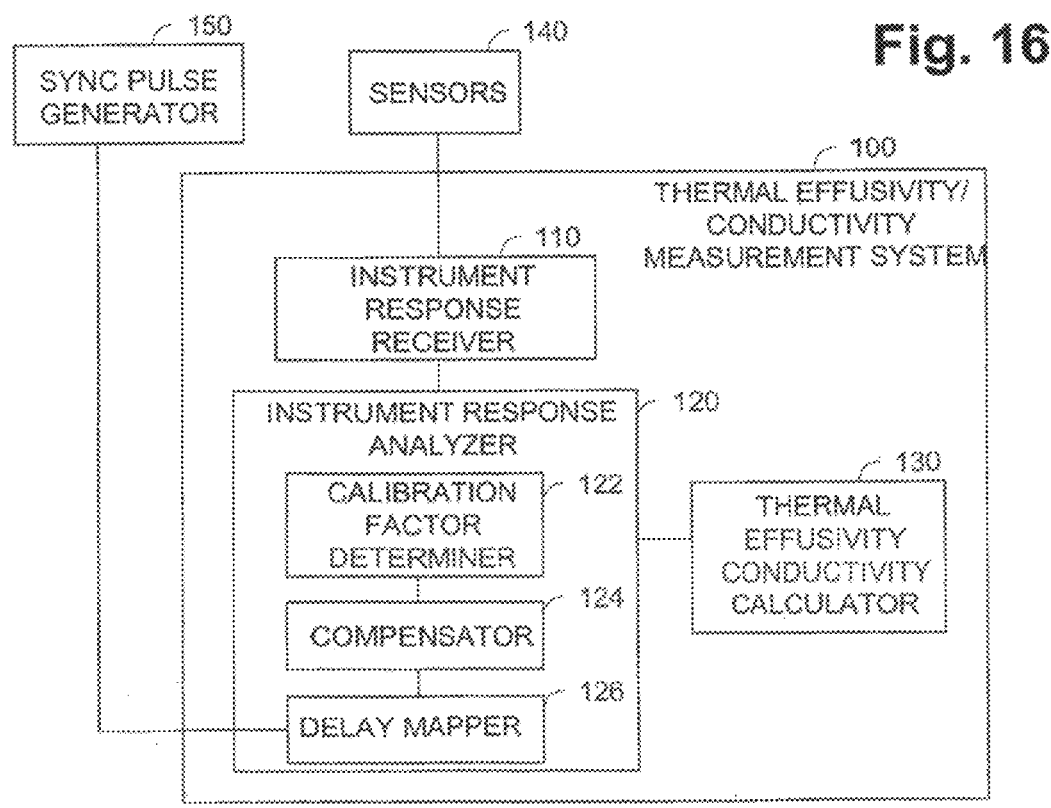
FIG. 16 there is illustrated a system for measuring thermal effusivity in accordance with an embodiment of the invention.

Referring to FIG. 16 there is illustrated a system for measuring thermal effusivity in accordance with an embodiment of the invention. The system 100 comprises an instrument response receiver 110, an instrument response analyzer 120 and a thermal effusivity calculator 130.

The instrument response receiver 110 receives instrument responses from a sensors 140. The instrument response analyzer 120 analyzes the received instrument responses. The thermal effusivity calculator 130 calculates thermal effusivity based on the output of the analyzer 120 as described herein above with regard to FIGS. 5-7.

The instrument response analyzer 120 has a calibration factor determiner 122 for determining a calibration factor, a compensator 124 for calibrating the sensor to compensate instrument responses by the calibration factor and a delay mapper 126 for determining sensor delay values referenced to a sync pulse from a synch pulse generator 150. The compensator also includes a fixed power algorithm to compensate for rising sensor temperature and therefore resistance.

The present invention has been described in the context of a mixing process and in particular a V blender mixing process having rotational motion. However, the present invention can be applied to any dynamic process having predictable patterns of motion, in which there exist relatively short periods (1-2 seconds) of relative stability between material and sensor. For example in addition to rotational motion, the motion can be oscillatory, pendular, rocking, i.e. generally periodic.

Numerous modifications, variations and adaptations may be made to the particular embodiments of the invention described above without departing from the scope of the invention, which is defined in the claims.

What is claimed is:

1. A method of monitoring a material during a dynamic process comprising the steps of:
   measuring thermal conductivity of the material during at least a portion of a cycle of the dynamic process;
   plotting a thermal conductivity curve over time;
   determining first and second inflection points on the thermal conductivity curve;
   determining a time delay value to the first inflection point and a measurement duration value between the first and second inflection points to determine an appropriate measurement period; and
   subsequently, measuring thermal conductivity of the material during the appropriate measurement period until a value of thermal conductivity indicative of a desired condition of the material is obtained.

2. A method as claimed in claim 1 wherein the dynamic process is mixing in a blender of at least two different materials and the cycle comprises a rotation in one or more directions.

3. A method as claimed in claim 2 wherein the portion of rotation is dependent upon one of blender fill percentage, rotation speed, material, and sensor position.

4. A method as claimed in claim 3 wherein the step of referencing includes the step of generating a timing signal corresponding to the appropriate measurement period.

5. A method as claimed in claim 4 wherein the dynamic process is one having predictable patterns of motion, in which there exist relatively short periods of relative stability of the material for measuring thermal conductivity.

6. Apparatus for monitoring a material during a dynamic process comprising:
   means for measuring thermal conductivity of the material during at least a portion of a cycle of a dynamic process;
   means for plotting a thermal conductivity curve over time;
   means for determining first and second inflection points on the thermal conductivity curve;
   means for determining a time delay value to the first inflection point and a measurement duration value between the first and second inflection points to determine an appropriate measurement period; and
   means for measuring thermal conductivity of the material during the appropriate measurement period until a value of thermal conductivity indicative of a desired condition of the material is obtained.

7. Apparatus as claimed in claim 6 wherein the dynamic process is mixing at least two different materials in a blender and the cycle comprises a rotation in one or more directions.

8. Apparatus as claimed in claim 7 wherein portion of rotation is dependent upon one of blender fill percentage, rotation speed, material, and sensor position.

9. Apparatus as claimed in claim 8 wherein the means for referencing includes means for generating a timing signal corresponding to the predetermined position within the cycle.

10. Apparatus as claimed in claim 6 wherein the means for measuring includes a plurality of sensors.

11. Apparatus as claimed in claim 10 wherein the means for measuring includes means for reading the plurality of sensors simultaneously.

12. Apparatus as claimed in claim 10 wherein the plurality of sensors includes a plurality of groups of sensors.

13. Apparatus as claimed in claim 10 wherein the plurality of sensors includes a first group of sensors positioned for reading during a first portion within the cycle and a second group of sensors positioned for reading during a second portion within the cycle different from the first.

14. Apparatus as claimed in claim 13 wherein the means for measuring includes means for reading each group of sensors simultaneously.

* * * * *